United States Patent
Sjogren

(10) Patent No.: US 7,936,277 B2
(45) Date of Patent: May 3, 2011

(54) APPARATUS AND METHOD FOR WIDTH DETECTION

(75) Inventor: John F. Sjogren, Wichita, KS (US)

(73) Assignee: Spirit AeroSystems, Inc., Wichita, KS (US)

(*) Notice: Subject to any disclaimer, the term of this patent is extended or adjusted under 35 U.S.C. 154(b) by 427 days.

(21) Appl. No.: 12/238,659

(22) Filed: Sep. 26, 2008

(65) Prior Publication Data
US 2010/0079297 A1 Apr. 1, 2010

(51) Int. Cl.
*G08B 21/00* (2006.01)

(52) U.S. Cl. ............ 340/675; 250/559.24; 250/559.36; 340/600; 356/635; 356/637; 356/237.1; 382/141; 382/286

(58) Field of Classification Search .......... 250/559.07–559.36; 156/64, 160, 156/167, 168, 169, 235; 356/635–637, 237.1; 382/141, 173, 286; 340/673–676, 600
See application file for complete search history.

(56) References Cited

U.S. PATENT DOCUMENTS

| | | | | |
|---|---|---|---|---|
| 2,791,931 A | * | 5/1957 | Summerhayes, Jr. | 356/637 |
| 3,586,445 A | * | 6/1971 | Martin, Jr. | 356/429 |
| 3,746,451 A | * | 7/1973 | Croissant et al. | 356/637 |
| 4,033,697 A | | 7/1977 | Pfoutz et al. | |
| 4,384,303 A | * | 5/1983 | Brenke et al. | 348/139 |
| 4,499,383 A | | 2/1985 | Loose | |
| 4,559,451 A | * | 12/1985 | Curl | 250/559.36 |
| 5,120,976 A | | 6/1992 | Clayton et al. | |
| 5,389,789 A | * | 2/1995 | Nguyen | 250/341.1 |
| 6,635,895 B2 | * | 10/2003 | Haque et al. | 250/559.36 |
| 2008/0055591 A1 | * | 3/2008 | Walton | 356/237.1 |

* cited by examiner

*Primary Examiner* — Brent Swarthout
(74) *Attorney, Agent, or Firm* — Hovey Williams LLP

(57) ABSTRACT

An apparatus and method for detecting a difference in width of a strip of material from a desired width of material. The apparatus may comprise a light source, a light detector, an alarm, a first fiber optic cable coupled with the light source, a second fiber optic cable coupled with the light detector, and a housing. The housing may comprise a material slot for passing the strip of material therethrough such that edges of the strip of material may at least partially intersect a plurality of light fields directed from the first fiber optic cable to the second fiber optic cable. The amount of light detected by the light detector is dependant on the amount of light blocked by the strip of material. If the amount of light received is outside of a range of tolerance from the desired width of material, the alarm may be actuated.

21 Claims, 8 Drawing Sheets

APPARATUS AND METHOD FOR WIDTH DETECTION

BACKGROUND

1. Field

The present invention relates to a system and method for sensing a change in a width of a strip of material from a desired width. More particularly, the present invention relates to a sensor that detects more light when the strip of material is narrower, and less light when the strip of material is wider.

2. Related Art

Composite tape strips are used to form composite parts, such as those used in the manufacture of aircrafts. In a lay-up process, strips of the composite tape are applied to a surface, layered, and then cured by pressure and heat to form a strong, light-weight composite part. Varying widths of composite tape strips may cause gaps or overlaps between adjacent tape strips. Gaps and/or overlaps can negatively affect the structural integrity of the composite part. Therefore, monitoring the width of composite tape strips may be useful during the manufacturing of a composite part to determine if the composite tape strip's width has varied from a desired value.

U.S. Pat. No. 4,033,697) (hereinafter the '697 patent) discloses one method for monitoring the width of strips of material. The '697 patent discloses monitoring the width of a hot strip of material, such as steel or glass, by using two sensing devices located above the strip and spaced apart a distance to provide viewing of each edge of the strip. The strip edges are imaged onto the detectors using visible and infrared radiation from the hot strips. Edge position information is determined for each edge. The edge position information is combined with a fixed dimension between the two sensing devices to calculate a total strip width. Unfortunately, the method disclosed in the '697 patent is relatively inexact. Additionally, the sensors disclosed in the '697 patent are cameras, which are quite large, limiting the locations within a strip-placement apparatus at which these sensors may be placed.

U.S. Pat. No. 5,120,976 (hereinafter the '976 patent) discloses a strip lay-up verification system with width determination. The system includes a sensor component having two edge detectors positioned on one side of a surface on which adjacent strips of material are laid. The system also includes a contrasting surface having different reflective properties than the strips of material. Each edge detector includes an illuminating device, comprising two arrays of LEDs, for illuminating an area including an edge of the strip of material. Each edge detector also includes an array of gradient refractive index lenses, which are fiber-optic devices having known focusing characteristics. The imaging device may be used for detecting the light reflected by an illuminated area and generating edge image signals from the detected light.

While the system disclosed in the '976 patent may be smaller than the system disclosed in the '697 patent, it is still limited in how small it may be manufactured, particularly because two edge detectors, each with two arrays of LEDs are required. Additionally, the angled configuration of the LED arrays, as illustrated in FIG. 1 of the '976 patent, may also limit how small such a device may be. Also, such a design may suffer from inaccurate readings due to errant reflections.

Accordingly, there is a need for an improved material width detector that overcomes the limitations of the prior art.

SUMMARY

The present invention provides a width detection apparatus and method for determining when a strip of material varies from a desired width. The strip of material may have a first edge, a second edge, a first face, and a second face. The apparatus may comprise an amplifier, a first fiber optic cable, a second fiber optic cable, and a housing for fixing the first fiber optic cable in spaced relationship with the second fiber optic cable such that the first fiber optic cable may direct light into the second fiber optic cable.

The amplifier may include a light source, a light detector, and an alarm having a first state and a second state. Light from the light source may be sent through the first fiber optic cable which is positioned to direct light into the second fiber optic cable. Then the light may be transmitted through the second fiber optic cable to the light detector. The alarm will be in a first state if an amount of light received by the light detector is equal to or with a predetermined range of tolerance from a desired amount of light. Otherwise, the alarm will be in a second state. For example, the second state may produce a visible, audible, or electrical signal to a user or an automated system. The desired amount of light corresponds with a desired width of material.

The first fiber optic cable may have a first end, a second end, and at least two optical fibers, each having a first end and a second end. The second fiber optic cable may have a first end, a second end, and at least two optical fibers, each having a first end and a second end. At least two optical fibers of the first fiber optic cable may be configured such that light extending from their second ends may form two light fields spaced apart from each other by a distance. The distance may be such that, if the strip of material is of the desired width, at least a portion of at least one of the light fields can shine on the first face of the strip of material at the first edge simultaneously while at least a portion of another one of the light fields shines on the first face of the strip of material at the second edge. The first fiber optic cable may be configured such that a first portion of its optical fibers are aligned to direct light into a first portion of optical fibers of the second fiber optic cable, and a second portion of its optical fibers are aligned to direct light into a second portion of optical fibers of the second fiber optic cable. The first edge of the strip of material may intersect the light field extending from the first portion of optical fibers of the first fiber optic cable and the second edge of the strip of material may intersect the light field extending from the second portion of the optical fibers of the first fiber optic cable.

The housing may fix the second ends of the optical fibers of the first fiber optic cable and the second ends of the optical fibers of the second fiber optic cable in spaced relationship to each other such that light from the second end of the first fiber optic cable may be received by the second end of the second fiber optic cable. The housing may further comprise inwardly facing walls forming a material slot through which the strip of material may be placed.

Alternatively, the fiber optic cables may be replaced with a first light source, a second light source, a first light detector, and a second light detector fixed within the housing such that light extending from the first light source may be at least partially received by the first light detector and light extending from the second light source may be at least partially received by the second light detector when the strip of material is of the desired width and centered between the first and second light sources and the first and second light detectors. In this embodiment of the invention, the first and second light sources and the first and second light detectors may be electrically connected to electronics configured to actuate the light sources, determine the amount of light received by the light detectors, and actuate the alarm to the second state if the amount of light received by the light detectors is not equal to or with a predetermined range of tolerance from the desired amount of light.

The method of determining when the strip of material varies from the desired width may comprise placing the strip of material in the material slot and sending light through the optical fibers of the first fiber optic cable. The method may further comprise receiving a portion of the light from the first fiber optic cable not blocked by the strip of material and transmitting light from the second fiber optic cable to the light detector. The method may also comprise determining if the amount of light detected is equal to or within the range of tolerance of the desired amount of light corresponding to the desired width of the strip of material, and outputting an audible, visual, or electrical alarm signal to a user or an automated system if the amount of light detected is not within the range of tolerance.

These and other important aspects of the present invention are described more fully in the detailed description below.

BRIEF DESCRIPTION OF THE DRAWINGS

Embodiments of the present invention are described in detail below with reference to the attached drawing figures, wherein.

Figure 1:
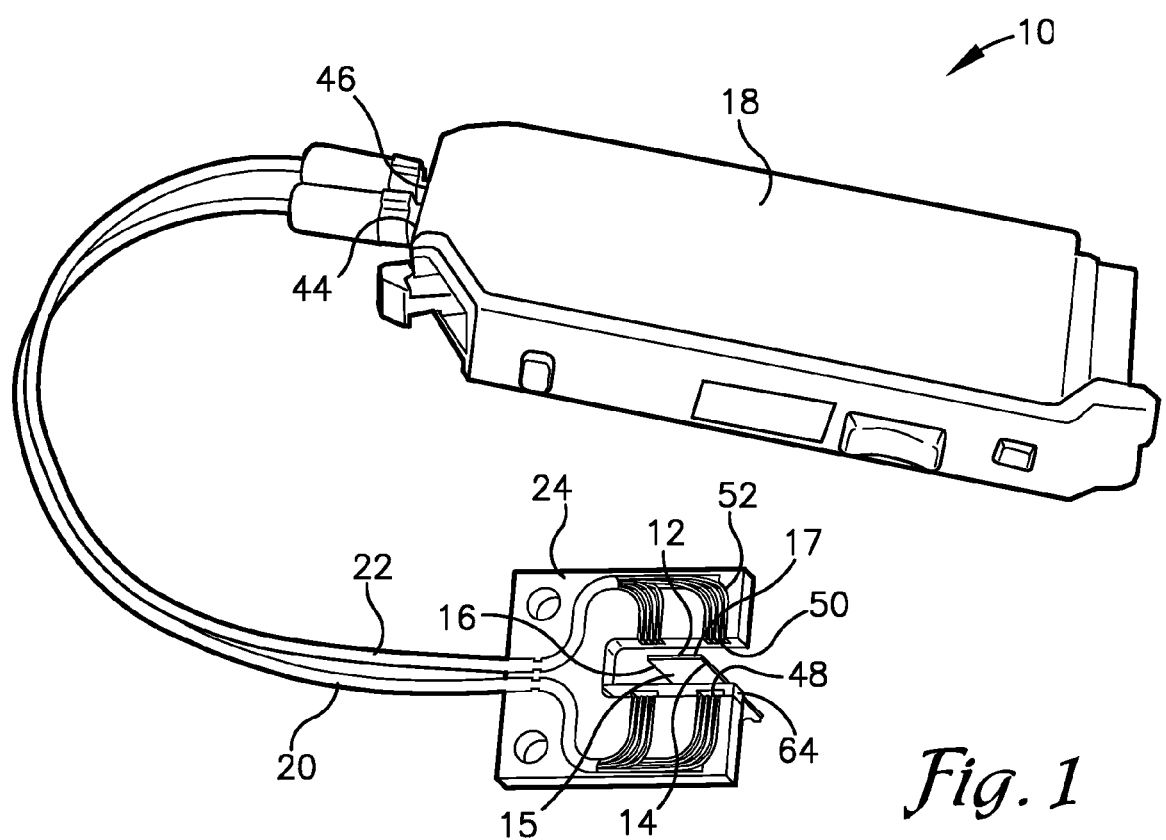
FIG. 1 is a perspective view of a width detection apparatus constructed in accordance with an embodiment of the present invention.

The drawing figure does not limit the present invention to the specific embodiments disclosed and described herein. The drawing is not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In accordance with various embodiments of the present invention, FIG. 1 illustrates a width detection apparatus 10 for detecting a change in width of a strip of material 12 from a desired width. The strip of material 12 may have a first edge 14, a second edge 16 opposite of the first edge 14, a first face 15, and a second face 17 opposite of the first face 15. The strip of material 12 may be any material such as composite tape, ribbons, glass, metal, plastic, etc. The width detection apparatus 10 may comprise an amplifier 18, a first fiber optic cable 20 coupled to the amplifier 18, a second fiber optic cable 22 coupled to the amplifier 18, and a housing 24 for fixing the fiber optic cables 20,22 in a spaced relationship to each other such that light from the first fiber optic cable 20 may be received by the second fiber optic cable 22.

Figure 2:
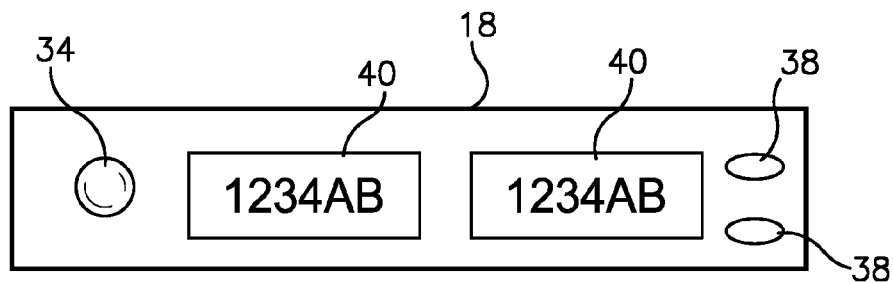
FIG. 2 is a top plan view of an amplifier of the width detection apparatus of FIG. 1.
Figure 3:
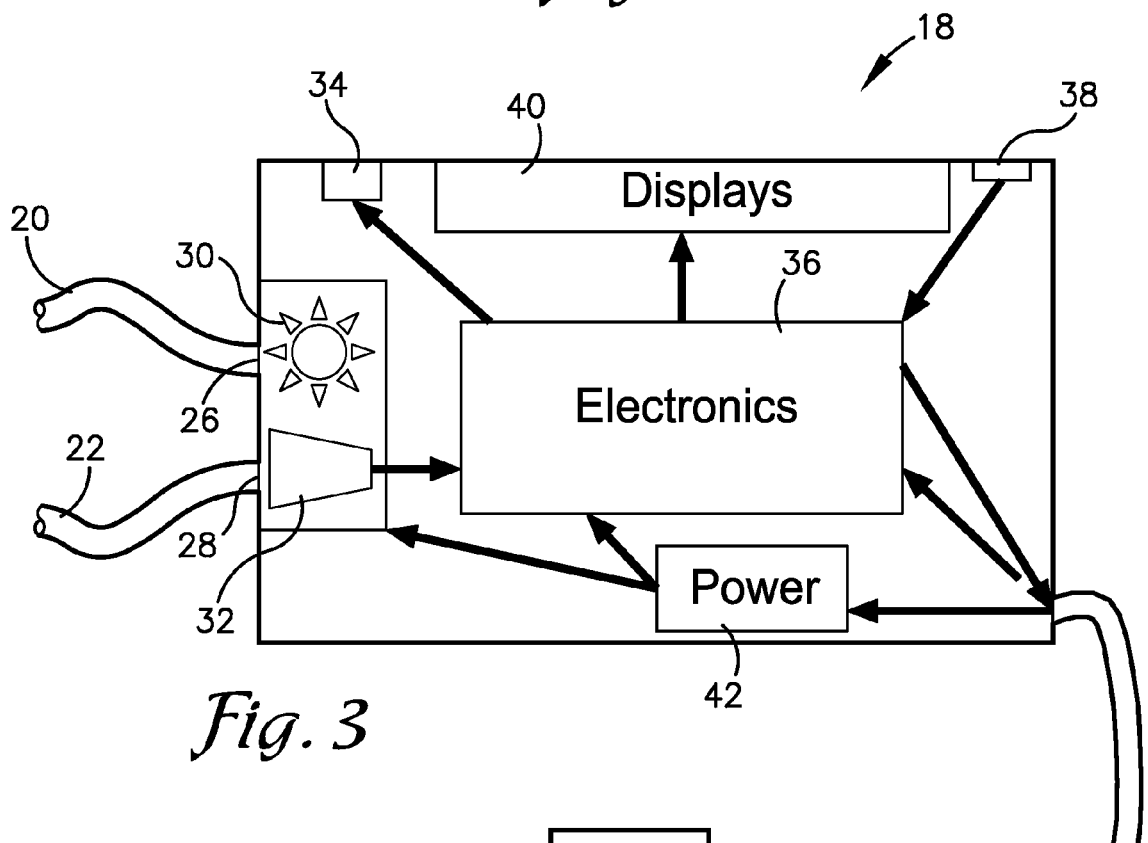
FIG. 3 is a schematic view of the amplifier of FIG. 2.
Figure 4:
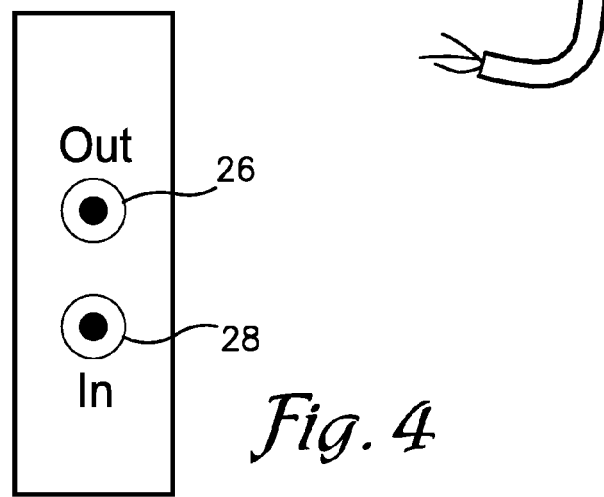
FIG. 4 is a side view of the amplifier of FIG. 2.

The amplifier 18 may be any apparatus for sending and receiving light and outputting a response based on the amount of light received. Additionally, the amplifier 18 may be any apparatus for sending and receiving light over fiber optic cables. For example, as illustrated in FIGS. 2-4, the amplifier 18 may include an output 26, an input 28, a light source 30, a light detector 32, an alarm 34 having a first state and a second state, and one or more electrical hardware components 36. For example, in one embodiment of the invention, the amplifier 18 may be the KEYENCE FS-V30 amplifier. The amplifier 18 may be of any size. However, in various embodiments of the invention, the amplifier 18 may have a width of between 1 inch and 10 inches, a height of between 0.3 inches and 8 inches, and a thickness of between 0.05 inches and 3 inches. Furthermore, the amplifier 18 may have a width of between 2 inches and 4 inches, a height of between 0.5 inches and 3 inches, and a thickness of between 0.2 inches and 0.6 inches. Specifically, the amplifier 18 may further have a width of between 2.5 and 3.5 inches, a height of between 1 inch and 2 inches, and a thickness of between 0.3 inches and 0.5 inches.

The light source 30 may send light out through the output 26 of the amplifier 18 and may be any light emitter known in the art for transmitting light through fiber optic cables. For example, the light source 30 may be laser diodes, LEDs, etc.

The light detector 32 may receive light through the input 28 of the amplifier 18 and may be any light detector 32 known in the art for turning light signals into electrical signals. For example, the light detector 32 may be a photo resistor, a photo cell, photo transistor, photo diode such as a silicon PIN photodiode, etc. As described herein, the electrical hardware components 36 may compare the actual amount of light received by the light detector 32 with a desired amount of light and trigger the alarm 34 if the actual amount of light received is not within a pre-determined range of tolerance from the desired amount of light. For example, the predetermined range of tolerance may be T−A to T+A, where T equals a pre-determined tolerance and A equals the desired amount of light.

The alarm 34 may be any device known in the art that is operable to change from a first state to a second state depending on the input it receives. For example, the alarm 34 may produce an audible, visual, or electrical signal to notify a user or a computing device that the actual amount of light detected by the light detector 32 of the amplifier 18 is not within the pre-determined range of tolerance. Specifically, when the amount of light detected deviates from the desired amount of light by more than the pre-determined tolerance, the electronic hardware components 36 may send an electrical signal to the alarm 34 to change the state of the alarm 34 from a first state to a second state. For example, the first state of the alarm 34 may be a state in which the alarm 34 is off, and the second state of the alarm 34 may be a state in which the alarm 34 is on.

The electrical hardware components 36 may be any number and combination of processors, controllers, integrated circuits, programmable logic devices, or other computing devices and resident or external memory for storing data. Specifically, the electrical hardware components 36 may be configured to receive a first electrical signal from the light detector 32 representing the actual amount of light detected and to compare the first electrical signal with a desired electrical signal representing the desired amount of light. Furthermore, the electrical hardware components 36 may be configured to send a signal commanding the alarm 34 to switch to the second state or to switch on if the first electrical signal is not within the pre-determined range of tolerance.

The amplifier 18 may also comprise a user interface 38 and one or more displays 40, all of which may be communicably coupled with the electrical hardware components 36. For example, the user interface 38 may allow a user to program into memory the desired amount of light to be received by the light detector 32, as well as the pre-determined tolerance or pre-determined range of tolerance. The user interface 38 may comprise one or more functionable inputs such as buttons, switches, scroll wheels, a touch screen associated with the displays, voice recognition elements such as a microphone, pointing devices such as mice, touchpads, tracking balls, styluses, a camera such as a digital or film still or video camera, combinations thereof, etc. Further, the user interface 38 may comprise wired or wireless data transfer elements such as a removable memory to enable the user and other devices or parties to remotely interface with the width detection apparatus 10.

The displays 40 may be one or more displays 40 coupled with the electrical hardware components 36 and may be operable to display various information corresponding to or determined by the amplifier 18, such as the actual amount of light detected, a percentage of the actual amount of light detected compared to the amount of light transmitted by the light source, the desired amount of light, the pre-determined range of tolerance, a desired width of the strip of material 12, whether the strip of material 12 is wider or narrower than desired, etc. The displays 40 may comprise conventional black and white, monochrome, or color display elements including CRT, TFT, LCD, and/or plasma display devices. The displays 40 may be integrated with the user interface 38, such as in embodiments where the displays 40 are touch-screen displays 40 to enable a user to interact with them by touching or pointing at display areas to provide information to the width detection apparatus 10.

The amplifier 18 may further comprise an internal or external power source 42. The power source 42 may provide electrical power to various components of the amplifier 18. For example, the power source 42 may be directly or indirectly coupled with the light source 30, the light detector 32, the electrical hardware components 36, the alarm 34, the user interface 38, and the displays 40. The power source 42 may comprise conventional power supply elements such as batteries, battery packs, etc. The power source 42 may also comprise power conduits, connectors, and receptacles operable to receive batteries, battery connectors, or power cables.

As illustrated in FIG. 1, the fiber optic cables 20,22 may be conduits through which light may be transmitted to and from the amplifier 18. For example, the first fiber optic cable 20 and the second fiber optic cable 22 may be any fiber optic cable known in the art and may each comprise a first end 44,46 and a second end 48,50, respectively, and one or more optical fibers 52, each having the same first end 44,46 and second end 48,50 as their corresponding fiber optic cable 20,22. The fiber optic cables 20,22 may be of conventional sizes and configurations. The first end 44 of the first fiber optic cable 20 may be coupled to the output 26 of the amplifier 18, such that the first fiber optic cable 20 may receive light from the light source 30. The second end 48 of the first fiber optic cable 20 may be positioned to direct light into the second end 50 of the second fiber optic cable 22. The first end 46 of the second fiber optic cable 22 may be coupled to the light detector 32 of the amplifier 18 to transmit light to the light detector 32.

As illustrated in FIG. 1 and FIGS. 5-10, the housing 24 may be formed of any substantially durable material, such as glass or plastic. For example, the housing 24 may be formed of polycarbonate resin thermoplastic such as LEXAN. Additionally, the housing 24 may be fabricated by solid freeform fabrication (SFF), rapid prototype methods, injection molding, or other traditional methods known in the art. In various embodiments of the invention, the housing 24 may be translucent, such that light may travel through at least a portion of the housing 24. The housing 24 may be any size. However, in various embodiments of the invention, the housing 24 may have a length and/or width of between 0.25 inches and 1 inch, and a thickness of between 0.01 inches and 0.5 inches. The housing 24 may further have a length and/or width of between 0.5 inches and 0.8 inches, and a thickness of between 0.025 inches and 0.2 inches.

Figure 6:
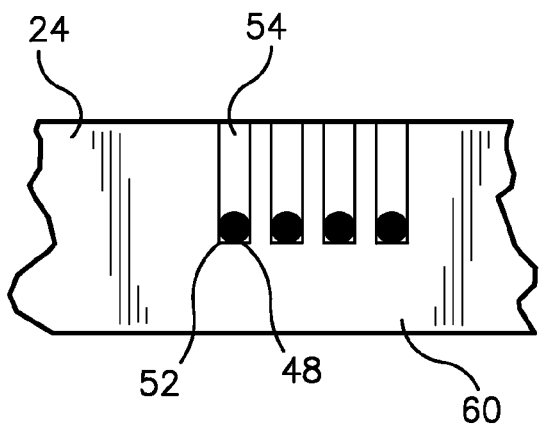
FIG. 6 is a sectional view of an inwardly facing wall of the housing of FIG. 5.
Figure 7:
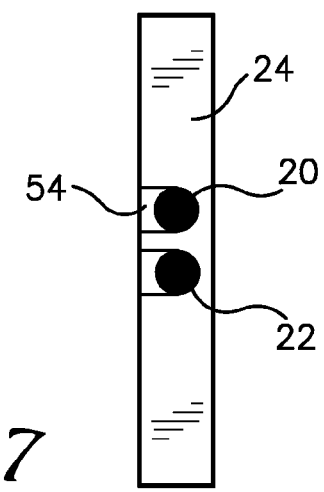
FIG. 7 is a side view of the housing of FIG. 5.
Figure 8:
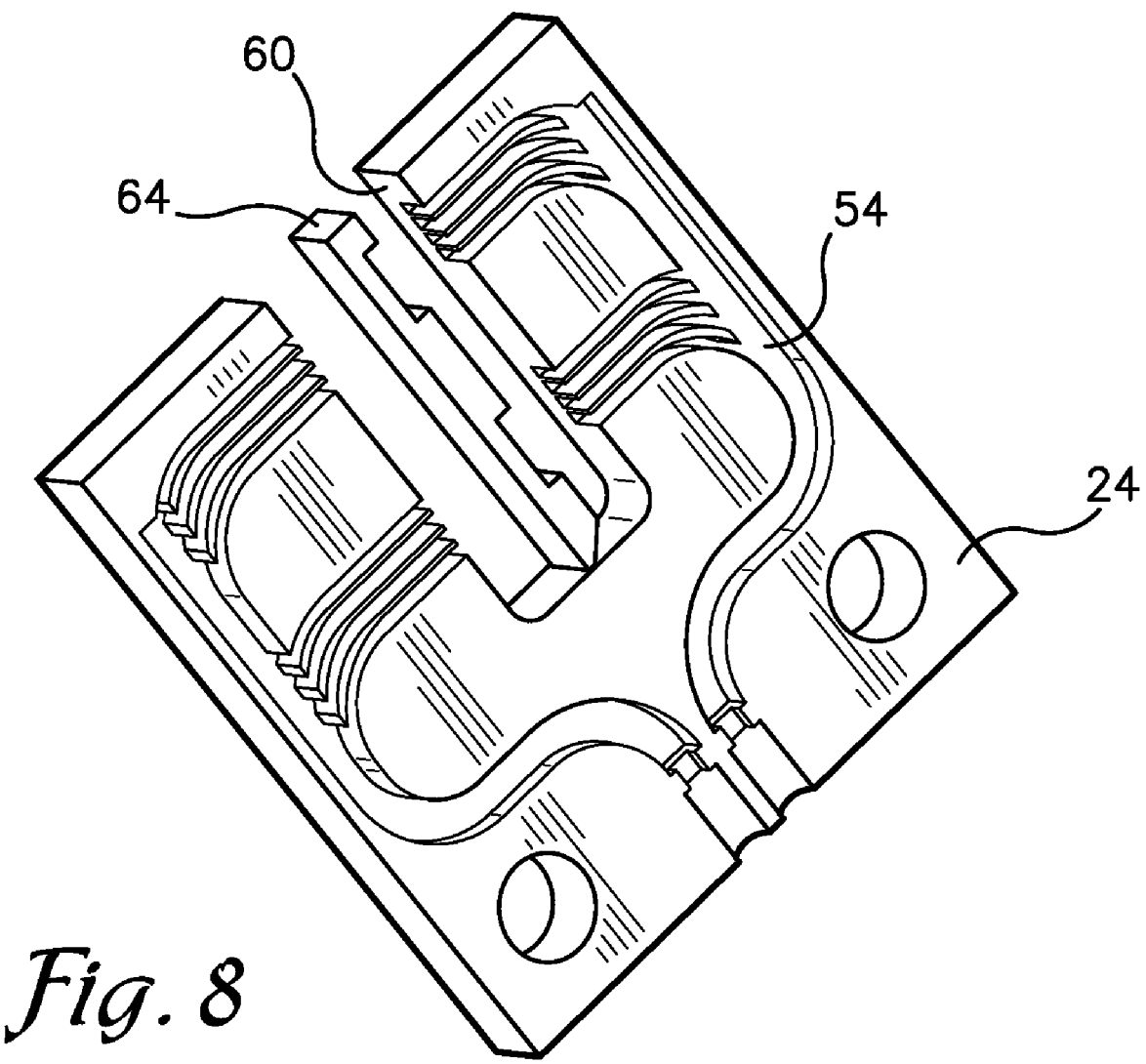
FIG. 8 is an exploded view of the housing of FIG. 5 including a diffuse lens for attaching to one of the inwardly facing walls of the housing.

The housing 24 may be formed around at least a portion of the first fiber optic cable 20 and the second fiber optic cable 22. For example, as illustrated in FIGS. 6-8, grooves 54 may be formed into the housing 24 in which the fiber optic cables 20,22 and individual optical fibers 52 may be placed. Specifically, the housing 24 may fix the second end 48 of the first fiber optic cable 20 and the second end 50 of the second fiber optic cable 22 in spaced relationship to each other such that light from the second end 48 of the first fiber optic cable 20 may be received by the second end 50 of the second fiber optic cable 22.

Figure 5:
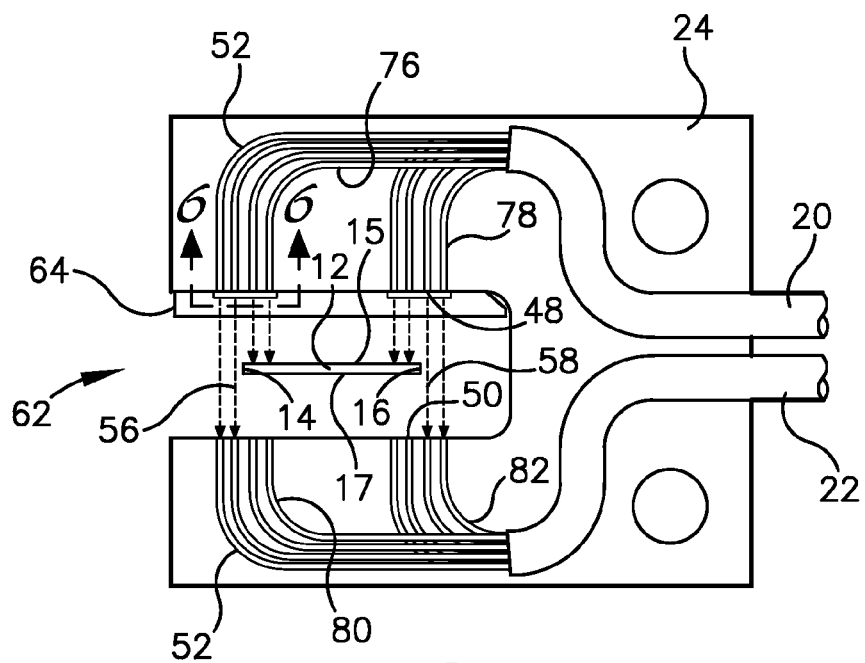
FIG. 5 is a sectional front elevation view of the housing and optical fibers of the width detection apparatus of FIG. 1 with beams of light shining on a first face of a strip of material at first and second edges of the strip of material.

Furthermore, the housing 24 may fix the individual optical fibers 52 of the first fiber optic cable 20 such that a plurality of light beams extending from the optical fibers 52 may diffuse through one or more diffuse lenses 64 to form two light fields 56,58, as illustrated in FIG. 5. The light fields 56,58 may be spaced apart from each other by a distance. The distance may be such that, if the strip of material 12 is of the desired width, at least a portion of at least one of the light fields 56 can shine on a portion of the first face 15 of the strip of material 12 at the first edge 14 simultaneously while at least a portion of another one of the light fields 58 shines on a portion of the first face 15 of the strip of material 12 at the second edge 16 of the strip of material 12, as depicted in FIG. 5. Each of the light fields 56,58 may be an area or region of diffused light, but is illustrated here by dash lines to demonstrate a portion of the light fields 56,58 being blocked by the strip of material 12. For example, in some embodiments of the invention, the light fields 56,58 may have centers that are spaced apart from each other by a distance equal to the desired width of the strip of material 12. So, for example, if the strip of material 12 of the desired width is placed in the path of the light fields 56,58, the center of one of the light fields 56 may intersect the first edge 14 of the strip of material 12, while the center of the other light field 58 intersects the second edge 16 of the strip of material 12.

The housing may additionally comprise inwardly facing walls 60 forming a material slot 62 through which the strip of material 12 may be placed. The material slot 62 may specifically be configured such that light from the first fiber optic cable 20 may pass through the material slot 62 in a general direction toward the first face 15 proximate the first and second edges 14,16 of the strip of material 12 when the strip of material 12 is positioned at a desired orientation. Within the material slot 62, the housing 24 may also be coupled to the one or more diffuse lenses 64 placed proximate the second ends 48,50 of one or both of the fiber optic cables 20,22 and configured to provide even fields of light as the light traverses the material slot 62, as depicted in FIGS. 1, 5, and 8.

Additionally, the diffuse lenses 64 may present the light from each of the optical fibers 52 of the first fiber optic cable 20 into the optical fibers 52 of the second fiber optic cable 22. The diffuse lenses 64 may be a frosted lens, a screen, paper, or any other material for diffusing light to diffuse a beam or beams of light such that matching fields of light are presented which may be centered at the edges 14,16 of the desired width of the strip of material 12.

Figure 9:
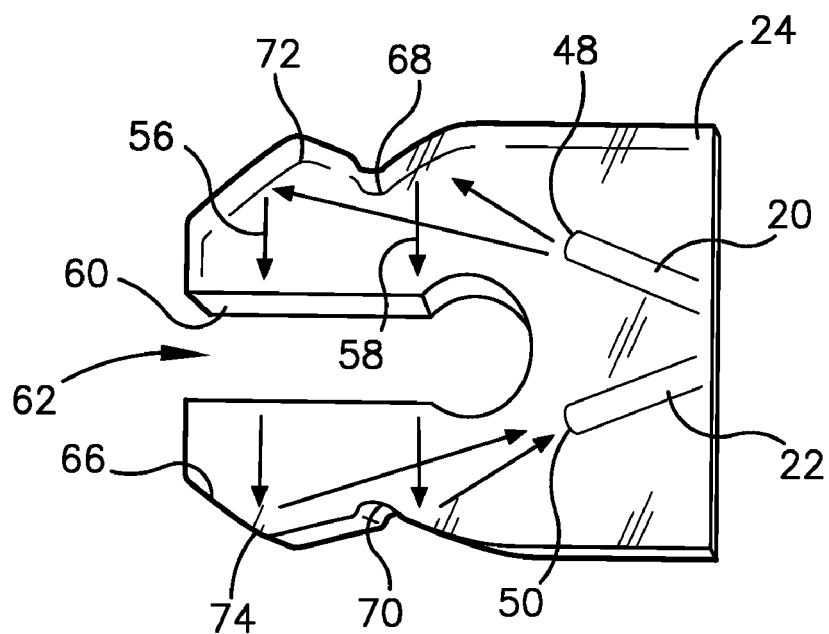
FIG. 9 is a front elevation view of two fiber optic cables and the housing of the width detection apparatus constructed in accordance with an embodiment of the present invention, illustrating the reflection of light within the housing.
Figure 10:
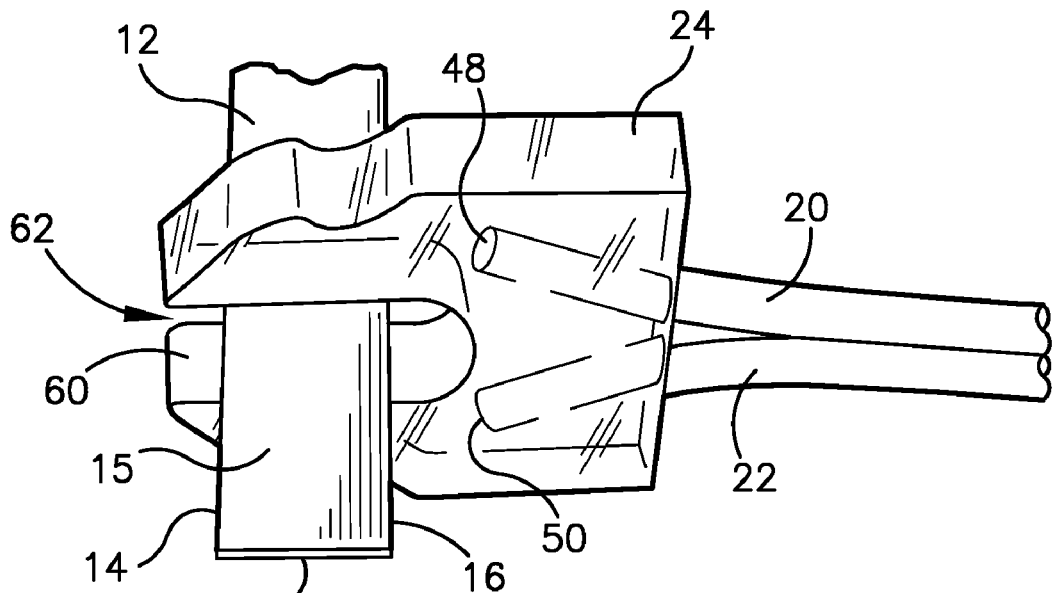
FIG. 10 is a perspective view of the housing of FIG. 9 illustrating the strip of material positioned therein.

In other various embodiments of the invention, as illustrated in FIGS. 9 and 10, the housing 24 may comprise a plurality of reflective surfaces 66 configured for directing light from the optical fibers 52 of the first fiber optic cable 20 to the optical fibers 52 of the second fiber optic cable 22. For example, the housing 24 may have various surface deviations 68,70,72,74 formed to reflect the light at particular angles. For example, one of the optical fibers 52 of the first fiber optic cable 20 may be aimed such that light reflects off of a portion of surface deviation 68, while another of the optical fibers 52 of the first fiber optic cable 20 may be aimed such that light reflects off of a portion of surface deviation 72.

Some of the surface deviations 68,72 may be configured to allow light to be directed through one of or a portion of the inwardly facing walls 60, through the material slot 62 then through another of or another portion of the inwardly facing walls 60. Then others of the surface deviations 70,74 may allow this light to reflect into the second fiber optic cable 22. The inwardly facing walls 60 may be coated or at least partially coated with some type of material for diffusing light, such as white paint, thereby forming the two light fields 56,58 for at least partially shining onto the strip of material 12, as described above. The coating may assist in balancing the light fields 56,58, and may be adjusted by adding or removing coating. The design illustrated in FIGS. 9 and 10 allows the second ends 48,50 of both fiber optic cables 20, 22 to be inserted into the housing 24 without individually routing the optical fibers 52, thereby saving assembly effort.

In various embodiments of the invention, as illustrated in FIG. 5, when at least a portion of the strip of material 12 is disposed within the material slot 62, a first portion 76 of the optical fibers 52 of the first fiber optic cable 20 are positioned to shine light on and/or proximate to the first edge 14 of the strip of material 12 and/or the first face 15 of the strip of material 12. Furthermore, a second portion 78 of the optical fibers 52 of the first fiber optic cable 20 are positioned to shine light on and/or proximate to the second edge 16 of the strip of material 12 and/or the first face 15 of the strip of material 12. Specifically, when the strip of material 12 is properly oriented in the material slot 62, at least some of the first portion 76 of optical fibers 52 of the first fiber optic cable 20 may be directed to shine light onto the first edge 14 and/or the first face 15 of the strip of material 12 and at least some of the second portion 78 of optical fibers 52 of the first fiber optic cable 20 may be directed to shine light onto the second edge 16 and/or the first face 15 of the strip of material 12.

Therefore, prior to inserting the strip of material 12 into the material slot 62, light from each of the optical fibers 52 of the first fiber optic cable 20 may be transmitted across the material slot 62 into the optical fibers 52 of the second fiber optic cable 22. For example, when the strip of material 12 is not inserted into the material slot 62, light from the first portion 76 of the optical fibers 52 of the first fiber optic cable 20 may be transmitted to a first portion 80 of the optical fibers 52 of the second fiber optic cable 22 and light from the second portion 78 of the optical fibers 52 of the first fiber optic cable 20 may be transmitted to a second portion 82 of the optical fibers 52 of the second fiber optic cable 22. This total light received by the second fiber optic cable 22 without the strip of material 12 in the material slot 62 may be used for comparison to determine how much of the light is then blocked by the strip of material 12 when it is placed in the material slot 62.

Because the light detector 32 receives the total light sensed by the optical fibers 52 of the second fiber optic cable 22, slight deviations in the position of the strip of material 12 will not adversely affect the results. This is because if the strip of material 12 shifts slightly, blocking more of the light transmitted from the first portion 76 of optical fibers 52, it will subsequently block less light from the second portion 78 of optical fibers 52, which will result in the same amount of light as if the edges 14,16 of the strip of material 12 are perfectly centered with the first portion 76 and the second portion 78 of the optical fibers 52 of the first fiber optic cable 20, respectively.

Figure 11:
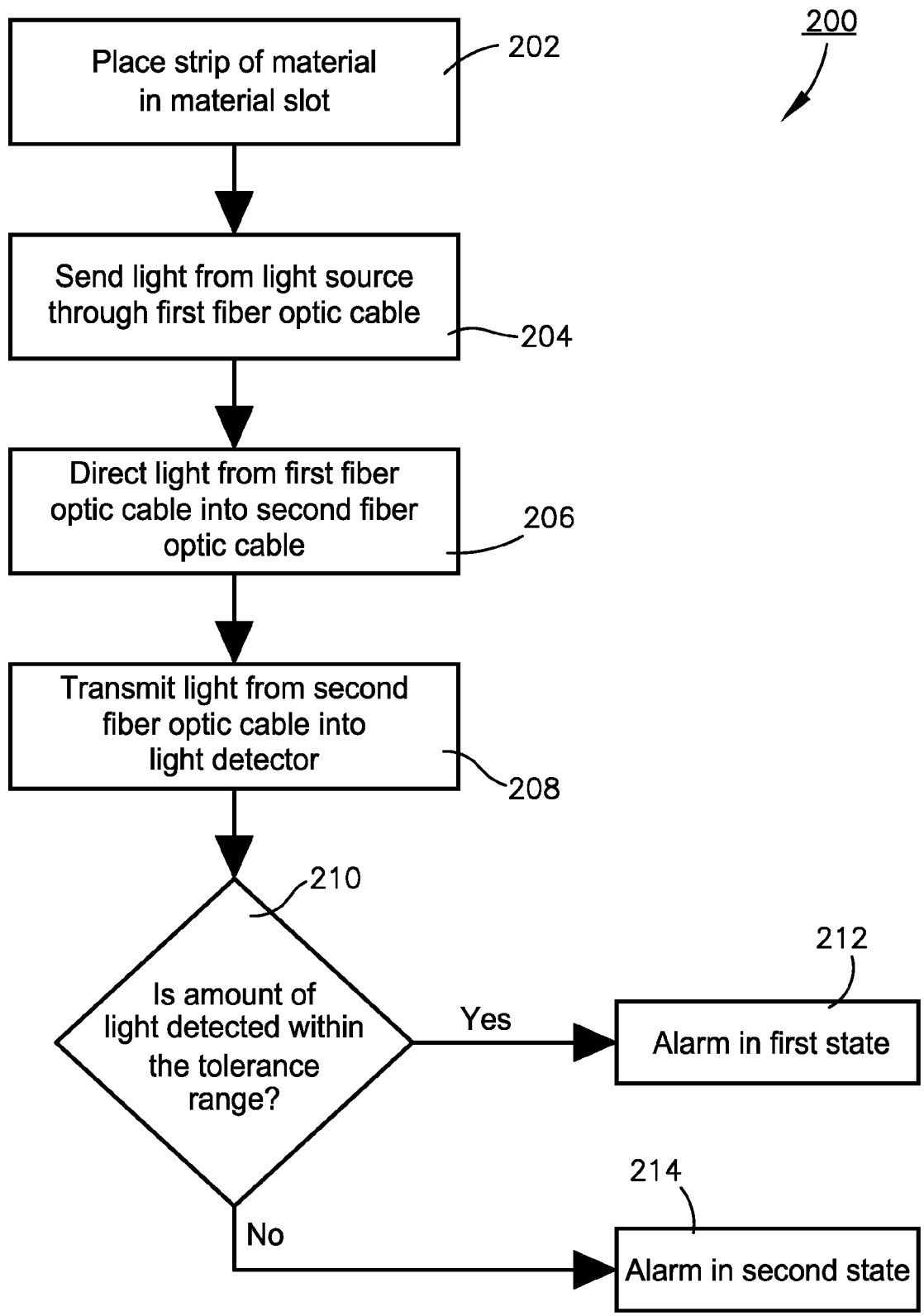
FIG. 11 is a flow chart of a method for detecting if the width of the strip of material deviates from a desired width using the width detection apparatus of FIG. 1.

In operation, the width detection apparatus 10 may be used to perform the method 200 illustrated in FIG. 11. For example, as depicted in step 202, the strip of material 12 may be placed in the material slot 62 according to the desired orientation. In the desired orientation, the light fields 56,58 from the first fiber optic cable 20 may be directed onto at least a portion of the first face 15 of the strip of material 12. Additionally, as depicted in step 204, the light source 30 may send light through the optical fibers 52 of the first fiber optic cable 20.

As depicted in step 206, the second fiber optic cable 22 may receive whatever portion of the light from the first fiber optic cable 20 is not blocked by the strip of material 12. The second fiber optic cable 22 may receive or detect light from a side of the strip of material 12 corresponding with the second face 17 of the strip of material 12. Light may be transmitted from the second fiber optic cable 22 to the light detector 32, as depicted in step 208, and the amplifier 18 may determine if the amount of light detected is within the pre-determined range of tolerance, as depicted in step 210.

If the amount of light detected is within the pre-determined range of tolerance, as depicted in step 212, the alarm 34 may be changed to or caused to remain in the first state. If the amount of light detected is not within the pre-determined range of tolerance, as depicted in step 214, the alarm 34 may be changed to or caused to remain in the second state.

So, for example, the alarm 34 may remain off if the strip of material 12 is of the desired width, but if the strip of material 12 is larger than the desired width, it will block more light. Therefore, less light will be detected by the light detector 32, and the alarm 34 may be activated by the amplifier 18 to turn on. Likewise, if the strip of material 12 is narrower than the desired width, less light will be blocked by the strip of material 12, more light will be detected by the light detector 32, and the alarm 34 may be activated by the amplifier 18 to turn on. This alarm 34 therefore may alert a user or an automated system that the width of the strip of material 12 is not of the desired width.

Additionally, the alarm 34 may alert the user or an automated system of twists, folds, or damage the strip of material 12. For example, if the strip of material 12 twists, it would not cover the same amount of width, and therefore more light would be allowed to pass through to the light detector 32, causing the alarm 34 to change to its second state. As discussed above, in the second state, the alarm 34 may provide a visual, audible or electrical signal to alert the user or the automated system.

Figure 12:
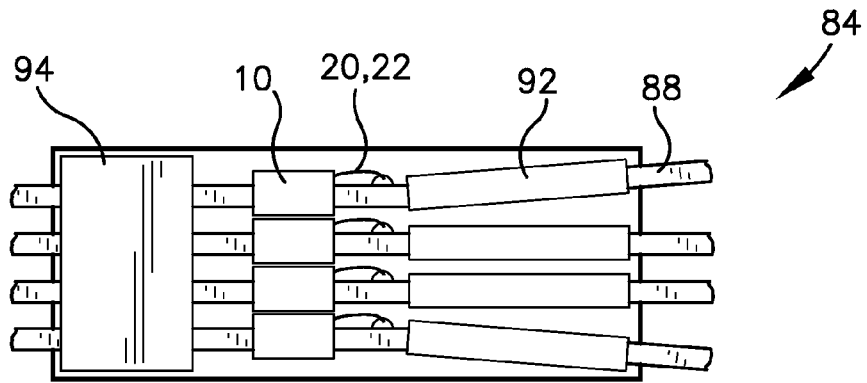
FIG. 12 is a sectional top plan view of an application head of a composite tape laying apparatus wherein a plurality of the width detection apparatuses of FIG. 1 are attached therein.
Figure 13:
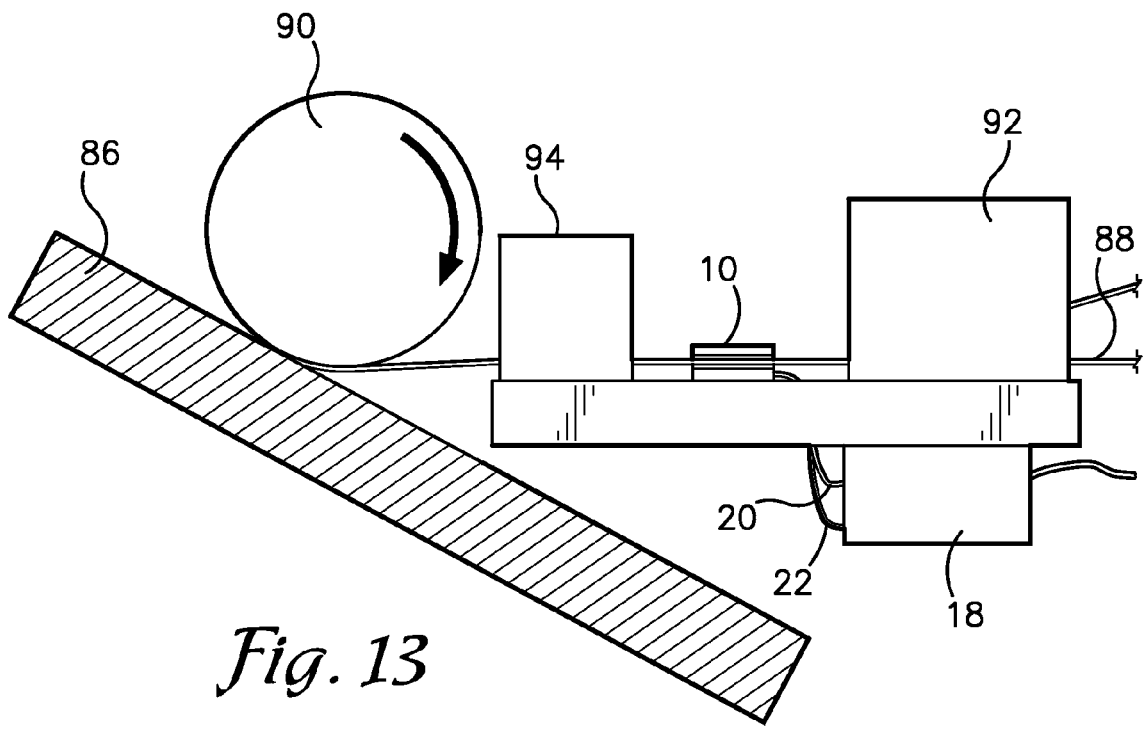
FIG. 13 is a sectional side elevation view of the application head of FIG. 12 including the width detection apparatuses attached therein.

The width detection apparatus 10 described above provides a number of benefits, particularly for applications where a small amount of space is available for such an apparatus. For example, as illustrated in FIGS. 12 and 13, within an application head 84 of a composite tape-laying apparatus for applying composite tape to a layup surface 86, a plurality of composite tape strips 88 may be fed to an application roller 90 through one or more composite tape directors 92 by one or more feed devices 94. The detection of composite tape width variation as close as possible to the end of its travel through the application head 84 may be desired to catch tow variations which may have been induced by its travel through the application head 84.

The application roller 90 typically applies the tape strips 88 adjacent one another, with only a strip-width's worth of space therebetween, such as a quarter inch between adjacent tape strip edges. Therefore, an appropriate width sensor must fit in the limited space available there to detect the tape width variation within a few thousandths of an inch while not imposing upon the tow paths. In general, the prior art apparatuses for measuring the width of a strip of material are too large for use within the application head of a composite tape-laying apparatus.

But as can be seen in FIGS. 12 and 13, a plurality of the width detection apparatuses 10 of the present invention may be applied, for example, between the composite tape directors 92 and the feed devices 94. The width detection apparatuses 10 may be adjacent one another, and the amplifiers 18 may be positioned in any location with relation to the application head 84 which may be reached by routing the fiber optic cables 20,22 in a non-flexing route, typically within about 5 meters.

The width detection apparatus 10 also provides other benefits over the prior art. For example, because the width detection apparatus 10 utilizes individual optical fibers within the fiber optic cables 20,22, this design allows the two edges 14,16 of the strip of material 12 to be monitored without the use of two separate fiber optic cables sending light and two separate fiber optic cables receiving light. Therefore, because only one input and one output is required, a single amplifier may be used. Also, the width detection apparatus 10 requires a limited amount of computations. For example, the apparatus does not require adding or comparing the amount of light blocked at one edge of the strip of material 12 with the light blocked at the other edge of the strip of material 12. This is because the width detection apparatus 10 does not need to determine how much light is detected by each optical fiber 52, but rather how much total light is detected by the fiber optic cable 22, which corresponds with the total amount of light blocked by the strip of material 12.

Figure 14:
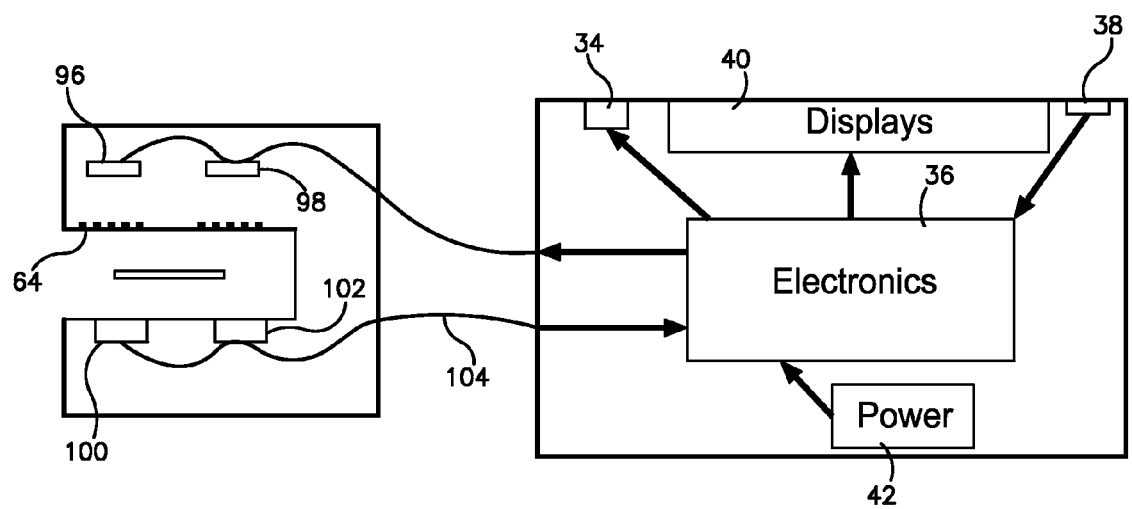
FIG. 14 is a schematic view of an alternative embodiment of the width detection apparatus of FIG. 1 without fiber optic cables.

In an alternative embodiment of the invention, illustrated in FIG. 14, the light source 30 and the light detector 32 may be fixed within or proximate to the housing 24 and may not require transmission through fiber optic cables 20,22. In this embodiment of the invention, ultra miniature light sources and sensors, as known in the art, may be used to maintain the small dimensions of the housing 24. Furthermore, the light source 30 may comprise a first light source 96 and a second light source 98 and the light detector 32 may comprise a first light detector 100 and a second light detector 102, such that each edge 14,16 of the strip of material 12 may be associated with one of the first and second light sources 96,98 and one of the first and second light detectors 100,102. For example, light extending from the first light source 96 may be at least partially received by the first light detector 100 and light extending from the second light source 98 may be at least partially received by the second light detector 102 when the strip of material 12 is of the desired width and centered between the first and second light sources 96,98 and the first and second light detectors 100,102.

In the embodiment of the invention illustrated in FIG. 14, the first and second light sources 96,98 and the first and second light detectors 100,102 may be electrically connected by any means known in the art, such as electrical cables 104, to electrical hardware components 36. The electrical hardware components 36 may be configured to actuate the first and second light sources 96,98, determine the amount of light received by the first and second light detectors 100,102, and actuate the alarm 34 to the second state if the amount of light received by the first and second light detectors 100,102 is not equal to or within a predetermined range of tolerance from the desired amount of light.

Although the invention has been described with reference to the embodiments illustrated in the attached drawings, it is noted that equivalents may be employed and substitutions made herein without departing from the scope of the invention as recited in the claims. For example, steps illustrated in the method 200 may be performed in a different order than described herein without departing from the scope of the invention. Additionally, the amplifier 18 may have more or less components than described herein and its components may or may not be physically coupled and/or housed physically together.

Having thus described an embodiment of the invention, what is claimed as new and desired to be protected by Letters Patent includes the following:

The invention claimed is:
1. An apparatus for detecting a difference in a width of a strip of material from a desired width, the strip of material having a first edge, a second edge, a first face, and a second face, the apparatus comprising:
 a light detector;
 a first fiber optic cable having a first end, a second end, and at least two optical fibers, each having a first end and a second end, and configured to receive light at the first end of the first fiber optic cable;
 a second fiber optic cable having a first end, a second end, and at least two optical fibers, each having a first end and a second end, and configured to receive light from the second end of the first fiber optic cable and to transmit light to the light detector; and
 a housing for fixing the second end of the optical fibers of the first fiber optic cable and the second end of the optical fibers of the second fiber optic cable in spaced relationship to each other,
 wherein the at least two optical fibers of the first fiber optic cable are configured such that light extending from their second ends form light fields spaced apart from each other by a distance such that, if the strip of material is of the desired width, at least a portion of at least one of the light fields can shine on the first face at the first edge simultaneously while at least a portion of another one of the light fields shines on the first face at the second edge of the strip of material.

2. The apparatus of claim 1, further comprising an alarm having a first state and a second state, wherein the alarm is configured to change from a first state to a second state if the amount of light detected by the light detector is not within a predetermined range of tolerance from a desired amount of light corresponding to the desired width of the strip of material.

3. The apparatus of claim 1, wherein the space between the second end of the first fiber optic cable and the second end of the second fiber optic cable is sufficient to allow the strip of material to pass therebetween.

4. The apparatus of claim 1, wherein at least a portion of the housing is substantially translucent.

5. The apparatus of claim 4, wherein the housing comprises reflective surfaces configured for directing light from the optical fibers of the first fiber optic cable into the optical fibers of the second fiber optic cable.

6. The apparatus of claim 1, wherein the first fiber optic cable is configured such that a first portion of its optical fibers are aligned to direct light into a first portion of optical fibers of the second fiber optic cable, and a second portion of its optical fibers are aligned to direct light into a second portion of optical fibers of the second fiber optic cable.

7. The apparatus of claim 1, the housing further comprising inwardly facing walls forming a material slot through which the strip of material may be placed, wherein the optical fibers are configured such that light passes through the material slot onto the first face of the strip of material.

8. The apparatus of claim 1, further comprising diffuse lenses placed at the second end of at least one of the first and the second fiber optic cables.

9. A system for monitoring changes in width of any of a plurality of strips of composite tape within an application head of a composite tape-laying machine, the system comprising a plurality of the apparatuses of claim 1, wherein each apparatus is fixed within the application head relative to one of the plurality of strips of composite tape, and is configured to monitor the width of the strips of composite tape as each strip is fed out of the application head.

10. The apparatus of claim 1, wherein the housing has at least one of a length and a width between approximately 0.25 inches and 1 inch, and a thickness of between approximately 0.01 inches and 0.5 inches.

11. The apparatus of claim 1, wherein the housing has at least one of a length and a width between approximately 0.5 inches and 0.8 inches, and a thickness of between approximately 0.025 inches and 0.2 inches.

12. An apparatus for detecting a change in width of a strip of material having a first edge, a second edge, a first face, and a second face, from a desired width of material, the apparatus comprising:
   an amplifier including a light source, a light detector, and an alarm having a first state and a second state;
   a first fiber optic cable having a first end, a second end, and at least two optical fibers, each having a first end and a second end, and configured to receive light at the first end of the first fiber optic cable from the light source of the amplifier;
   a second fiber optic cable having a first end, a second end, and at least two optical fibers, each having a first end and a second end, and configured to transmit light from the first end of the second fiber optic cable to the light detector of the amplifier, wherein the at least two optical fibers of the first fiber optic cable are configured such that light extending from their second ends form light fields spaced apart from each other by a distance such that, if the strip of material is of the desired width, at least a portion of at least one of the light fields can shine on the first face of the strip of material at the first edge simultaneously while at least a portion of another one of the light fields shines on the first face of the strip of material at the second edge; and
   a housing for fixing the second end of the optical fibers of the first fiber optic cable and the second end of the optical fibers of the second fiber optic cable in spaced relationship to each other such that light from the second end of the first fiber optic cable may be received by the second end of the second fiber optic cable, the housing further comprising inwardly facing walls forming a material slot through which the strip of material may be placed,
   wherein the alarm is configured to change from a first state to a second state if the amount of light detected by the light detector of the amplifier is not within a predetermined range of tolerance from a desired amount of light corresponding to a desired width of the strip of material,
   wherein the first fiber optic cable is configured such that a first portion of its optical fibers are aligned to direct light into a first portion of optical fibers of the second fiber optic cable, and a second portion of its optical fibers are aligned to direct light into a second portion of optical fibers of the second fiber optic cable.

13. The apparatus of claim 12, wherein the space between the second end of the first fiber optic cable and the second end of the second fiber optic cable is sufficient to allow the strip of material to pass therebetween.

14. The apparatus of claim 12, wherein at least a portion of the housing is substantially translucent.

15. The apparatus of claim 14, wherein the housing comprises reflective surfaces configured for directing light from the optical fibers of the first fiber optic cable through the material slot and configured for further directing light to the optical fibers of the second fiber optic cable.

16. The apparatus of claim 12, further comprising diffuse lenses placed at the second end of at least one of the first and the second fiber optic cables.

17. A system for monitoring changes in width of any of a plurality of strips of composite tape within an application head of a composite tape-laying machine, the system comprising a plurality of the apparatuses of claim 12, wherein each apparatus is fixed within the application head relative to one of the plurality of strips of composite tape, and is configured to monitor the width of the strips of composite tape as each strip is fed out of the application head.

18. The apparatus of claim 12, wherein the housing has at least one of a length and a width between approximately 0.25 inches and 1 inch, and a thickness of between approximately 0.01 inches and 0.5 inches.

19. The apparatus of claim 12, wherein the housing has at least one of a length and a width between approximately 0.5 inches and 0.8 inches, and a thickness of between approximately 0.025 inches and 0.2 inches.

20. A method of determining a change in the width of a strip of material from a desired width, the method comprising:
   directing light extending from a first portion of optical fibers of a first fiber optic cable toward a first edge and a first face of the strip of material;
   directing light extending from a second portion of optical fibers of the first fiber optic cable toward a second edge and the first face of the strip of material;

detecting an amount of light from a side of the strip of material corresponding with a second face of the strip of material, which is opposite of the first face of the strip of material;

determining if the amount of light detected is within a range of tolerance of a desired amount of light corresponding to the desired width of the strip of material; and outputting an audible, visual, or electrical alarm signal to a user or an automated system if the amount of light detected is not within the range of tolerance.

21. An apparatus for detecting a difference in a width of a strip of material from a desired width, the strip of material having a first edge, a second edge, a first face, and a second face, the apparatus comprising:

a first light source;

a second light source;

a first light detector configured to receive light from the first light source;

a second light detector configured to receive light from the second light source;

an alarm having a first state and a second state; and electrical hardware components configured to actuate the first and second light sources, determine the amount of light received by the first and second light detectors, and actuate the alarm to the second state if the amount of light received by the first and second light detectors is not equal to or within a predetermined range of tolerance from the desired amount of light, wherein the strip of material is substantially centered between the first light source, the second light source, the first light detector, and the second light detector;

wherein the desired amount of light corresponds to the desired width of the strip of material, wherein the first and second light sources form light fields spaced apart from each other by a distance such that, if the strip of material is of the desired width, at least a portion of at least one of the light fields can shine on the first face of the strip of material at the first edge simultaneously while at least a portion of another one of the light fields shines on the first face of the strip of material at the second edge.

* * * * *